United States Patent
Miller et al.

(10) Patent No.: US 10,428,369 B2
(45) Date of Patent: Oct. 1, 2019

(54) ANALYZING MICRODROPLET OUTLINE SIZE AND ADJUSTING CHANNEL PRESSURE TO ALTER MICRODROPLET SIZE

(71) Applicant: Bio-Rad Laboratories, Inc., Hercules, CA (US)

(72) Inventors: Benjamin J. Miller, Littleton, MA (US); Qun Zhong, Lexington, MA (US); Darren Roy Link, Lexington, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 431 days.

(21) Appl. No.: 15/176,710

(22) Filed: Jun. 8, 2016

(65) Prior Publication Data
US 2016/0281140 A1 Sep. 29, 2016

Related U.S. Application Data

(63) Continuation of application No. 14/173,974, filed on Feb. 6, 2014, now abandoned, which is a continuation of application No. 13/554,655, filed on Jul. 20, 2012, now Pat. No. 8,658,430.

(60) Provisional application No. 61/509,837, filed on Jul. 20, 2011.

(51) Int. Cl.
| | | |
|---|---|---|
| *C12Q 1/6806* | (2018.01) | |
| *B05B 1/08* | (2006.01) | |
| *B05B 1/26* | (2006.01) | |
| *B05B 7/00* | (2006.01) | |
| *B01F 13/00* | (2006.01) | |
| *B01F 15/00* | (2006.01) | |
| *B01F 3/08* | (2006.01) | |
| *B05B 1/02* | (2006.01) | |

(Continued)

(52) U.S. Cl.
CPC .......... *C12Q 1/6806* (2013.01); *B01F 3/0807* (2013.01); *B01F 13/0062* (2013.01); *B01F 15/00357* (2013.01); *B01L 3/502761* (2013.01); *B01L 3/502784* (2013.01); *B05B 1/02* (2013.01); *B05B 1/08* (2013.01); *B05B 1/26* (2013.01); *B05B 7/0012* (2013.01); *B01L 7/525* (2013.01); *B01L 2200/025* (2013.01); *B01L 2200/0647* (2013.01); *B01L 2200/141* (2013.01); *B01L 2200/143* (2013.01); *B01L 2200/148* (2013.01); *B01L 2300/0867* (2013.01); *B01L 2300/14* (2013.01); *B01L 2400/0487* (2013.01); *Y10T 436/2575* (2015.01)

(58) Field of Classification Search
None
See application file for complete search history.

(56) References Cited

PUBLICATIONS

Song, Helen, Delai L. Chen, and Rustem F. Ismagilov. "Reactions in droplets in microfluidic channels." Angewandte chemie international edition 45.44 (2006): 7336-7356.*

* cited by examiner

*Primary Examiner* — G Steven Vanni
(74) *Attorney, Agent, or Firm* — Brown Rudnick LLP; Thomas C. Meyers (57) ABSTRACT

The invention generally relates to methods and systems for manipulating droplet size. In certain aspects, the invention provides methods for manipulating droplet size that include forming droplets of aqueous fluid surrounded by an immiscible carrier fluid, and manipulating droplet size during the forming step by adjusting pressure exerted on the aqueous fluid or the carrier fluid.

19 Claims, 7 Drawing Sheets

(51) Int. Cl.
*B01L 3/00* (2006.01)
*B01L 7/00* (2006.01)

ANALYZING MICRODROPLET OUTLINE SIZE AND ADJUSTING CHANNEL PRESSURE TO ALTER MICRODROPLET SIZE

RELATED APPLICATION

The present application is a continuation of U.S. Nonprovisional Ser. No. 14/173,974, filed Feb. 6, 2014, which is a continuation of U.S. Nonprovisional Ser. No. 13/554,655, filed Jul. 20, 2012, now U.S. Pat. No. 8,658,430, which claims benefit of and priority to U.S. Provisional No. 61/509,837, filed Jul. 20, 2011, the content of each is incorporated by reference herein in its entirety.

FIELD OF THE INVENTION

The invention generally relates to methods and systems for manipulating fluidic droplet size.

BACKGROUND

The ability to precisely manipulate fluidic streams enhances the use and effectiveness of microfluidic devices. Typically, networks of small channels provide a flexible platform for manipulation of small amounts of fluids. Certain microfluidic devices utilize aqueous droplets in an immiscible earner fluid. The droplets provide a well-defined, encapsulated microenvironment that eliminates cross contamination and changes in concentration due to diffusion or surface interactions.

Microfluidic devices for performing biological, chemical, and diagnostic assays generally include at least one substrate containing one or more etched or molded channels. The channels are generally arranged to form individual fluid circuits, each circuit including a sample fluid channel, an immiscible carrier fluid channel, and an outlet channel. The channels of each circuit may be configured such that they meet at a junction so that droplets of aqueous fluid surrounded by carrier fluid are formed at the junction and flow into the outlet channel. In some cases, the outlet channel of each circuit is connected to a main channel that receives all of the droplets from the different fluidic circuits and flows them to an analysts module. In other cases, the outlet channels connect to exit ports to carry the droplets to a collection vessel.

Since each fluidic circuit may have different samples, and because different compositions (e.g., concentration and/or length of nucleic acid) from different samples affect how droplets form, droplets of different sizes may be produced by each circuit. A problem with droplets of different sizes flowing through the same channel is that the droplets travel at different velocities. Droplets traveling at different velocities may cause unwanted collisions or unwanted coalescence of droplets in the channel. Thus it is important that individual fluidic circuits produce droplets of uniform size so that the droplets travel at the same velocity in the channel and do nor collide or coalesce in an unwanted manner.

Droplets are typically generated one at a time at a junction between an aqueous fluid and an immiscible earner fluid. Droplet volume and frequency (the number of droplet generated per unit time) are determined by geometrical factors such as the cross-sectional area of the channels at the junction and the fluidic properties such as the fluid viscosities and surface tensions as well as the infusion rates of the aqueous and carrier fluids. To control the volume of the aqueous droplet, within a range, droplet volume can be adjusted by tuning the oil infusion rate through the junction. This is readily achieved with a pressure regulator on the carrier fluid stream. In some cases it is desirable to have multiple junctions operating as separate circuits to generate droplets and have independent control over the oil infusion rates through each circuit. This is readily achieved by using separate pressure regulators for each aqueous stream and each carrier fluid stream. A simpler and lower cost system would have a single carrier oil source at a single pressure providing a flow of carrier oil through each system. The problem with such a system is that in adjusting the pressure to regulate the How of carrier oil in one circuit the carrier oil in all circuits would be effected and independent control over droplet volume would be compromised. Thus, it is important to have a means whereby at a fixed carrier oil pressure the flow of carrier oil in each of the circuits can be independently controlled to regulate droplet volume.

SUMMARY

The invention generally relates to methods and systems for manipulating droplet size. The invention recognizes that in a fluidic circuit, changing the pressure exerted on the aqueous phase changes the flow rate of the immiscible carrier fluid. Changing the flow rate of the immiscible fluid manipulates the size of the droplet. Thus, adjusting pressure, which changes flow rate, adjusts droplet size. Pressure adjustments may be made independent of one another such that the pressure exerted on the aqueous phase in individual fluidic circuits can be adjusted to produce droplets of uniform size from the different fluidic circuits. In this manner, droplets produced from different fluidic circuits travel at the same velocity in a main channel and do not collide or coalesce in an unwanted manner.

In certain aspects, the invention provides methods for manipulating droplet size that involve forming droplets of aqueous fluid surrounded by an immiscible carrier fluid, and manipulating droplet size during the forming step by adjusting pressure exerted on the aqueous fluid or the carrier fluid. Methods of the invention involve forming a sample droplet. Any technique known in the an for forming sample droplets may be used with methods of the invention. An exemplary method involves flowing a stream of sample fluid so that the sample stream intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets. The carrier fluid may be any fluid that is immiscible with the sample fluid. An exemplary carrier fluid is oil. In certain embodiments, the carrier fluid includes a surfactant, such as a fluorosurfactant.

Methods of the invention may be conducted in microfluidic channels. As such, in certain embodiments, methods of the invention may further involve flowing the droplet channels and under microfluidic control. Methods of the invention further involve measuring the size of a generated droplet. Any method known in the art may be used to measure droplet size. Preferable methods involve realtime image analysis of the droplets, which allows for a feedback loop to be created so that droplet size may be adjusted in real-time. In certain embodiments, measuring the droplet site is accomplished by taking an image of the droplet and measuring a midpoint of an outline of the droplet image, as opposed to measuring an inside or an outside of the droplet.

Another aspect of the invention provides methods for forming droplets of a target volume that include flowing an aqueous fluid through a first channel, flowing an immiscible carrier fluid through a second channel, forming an aqueous droplet surrounded by the carrier fluid, and adjusting resistance in the first or second channels during the forming step to adjust volume of the droplets, thereby forming droplets of a target volume.

Another aspect of the invention provides methods for forming substantially uniform droplets that involve flowing a plurality of different aqueous fluids through a plurality of different channels, flowing an immiscible carrier fluid through a carrier fluid channel, forming substantially uniform droplets of the different aqueous fluids, each droplet being surrounded by the carrier fluid, by independently adjusting resistance in the different channels.

Another aspect of the invention provides microfluidic chips that include a substrate, and a plurality of channels, in which at least two of the channels include pressure regulators, the pressure regulators being independently controllable. Generally, the plurality of channels include at least one aqueous fluid channel, at least one immiscible earner fluid channel, at least one outlet channel, and a main channel. In certain embodiments, the channels are configured to form microfluidic circuits, each circuit including an aqueous fluid channel, a carrier fluid channel, and an outlet channel. The channels of each circuit meet at a junction such that droplets of aqueous fluid surrounded by carrier fluid are formed at the junction and How into the outlet channel. Each outlet channel of each circuit is connected to the main channel. The channels may be etched or molded into the substrate. The channels may be open channels or enclosed channels. Droplets may be collected in a vessel on the device or off of the device.

Another aspect of the invention provides droplet systems that include a microfluidic chip dial include a substrate, and a plurality of channels, in which at least two of the channels include pressure regulators, the pressure regulators being independently controllable; and a pressure source coupled to the chip.

Other aspects and advantages of the invention are provided in the following description and claims.

DETAILED DESCRIPTION

The invention generally relates to methods and systems for manipulating droplet size. In certain aspects, the invention provides methods for manipulating droplet size that involve forming droplets of aqueous fluid surrounded by an immiscible carrier fluid, and manipulating droplet size during the forming step by adjusting pressure exerted on the aqueous fluid or the carrier fluid.

Droplet Formation

Methods of the invention involve forming sample droplets. In certain embodiments, the droplets include nucleic acid from different samples. In particular embodiments, each droplet includes a single nucleic acid template, a single protein molecule or single cell. The droplets are aqueous droplets that are surrounded by an immiscible carrier fluid. Methods of forming such droplets are shown for example in Link et al. (U.S. patent application numbers 2008/0014589, 2008/0003142, and 2010/0137163). Stone et al. (U.S. Pat. No. 7,708,949 and U.S. patent application number 2010/0172803). Anderson et al. (U.S. Pat. No. 7,041,481 and which reissued as RE41,780) and European publication number EP2047910 to Raindance Technologies Inc. The content of each of which is incorporated by reference herein in its entirety.

Figure 1:
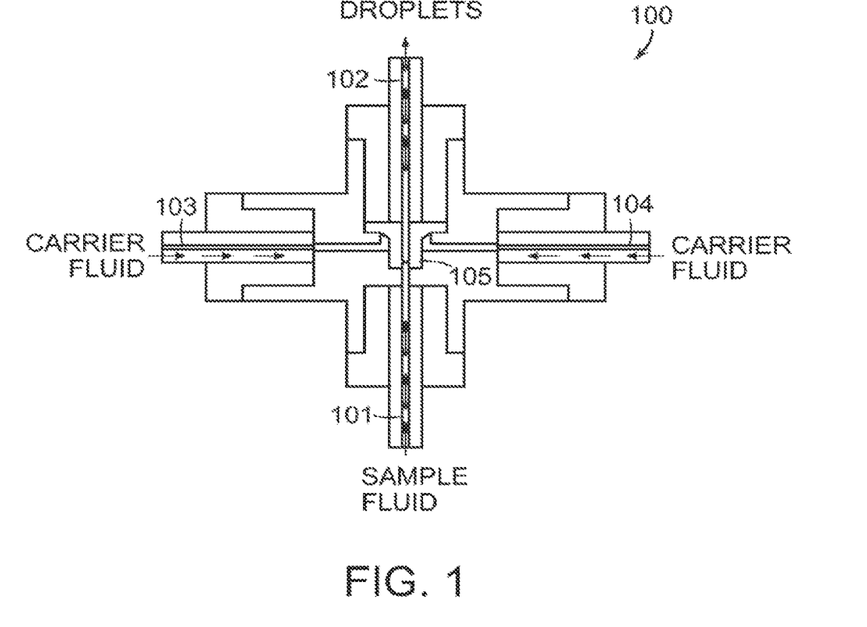
FIG. 1 is a drawing showing a device for droplet formation.
Figure 2:
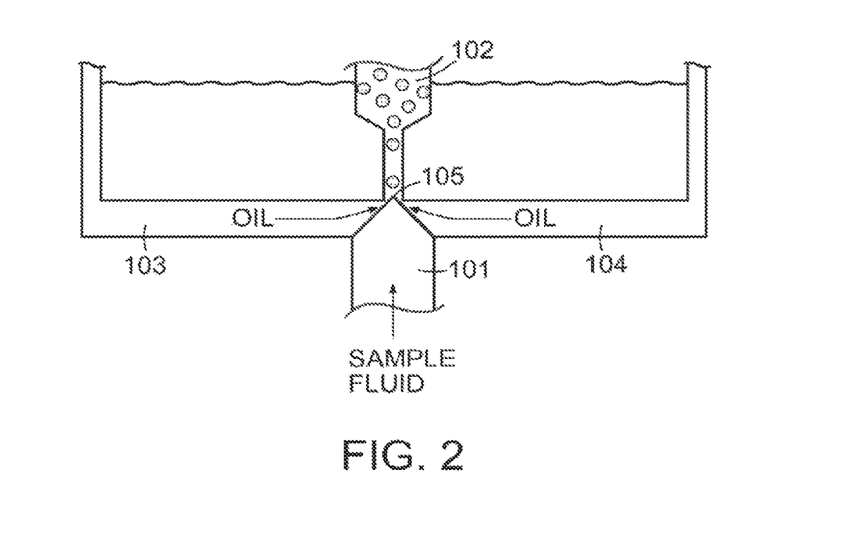
FIG. 2 is a drawing showing a device for droplet formation.

FIG. 1 shows an exemplary embodiment of a device 100 for droplet formation. Device 100 includes an inlet channel 101, and outlet channel 102, and two carrier fluid channels 103 and 104. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (See FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with enzymes can be used. The carrier fluid is one that is immiscible with the sample fluid. The carrier fluid can be a non-polar solvent, decane (e.g., tetradecane or hexadecane), fluorocarbon oil, silicone oil or another oil (for example, mineral oil).

In certain embodiments, the earner fluid contains one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid.

Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M), which then serves as the carrier fluid.

Manipulating Droplet Size

The invention recognizes that in a fluidic circuit, changing the pressure exerted on the aqueous phase changes the flow rate of the immiscible carrier fluid. Changing the flow rate of the immiscible fluid manipulates the size of the droplet. Thus, adjusting pressure, which changes flow rate, adjusts droplet size. Pressure adjustments may be made independently of each other such that die pressure exerted on the aqueous phase in individual fluidic circuits can be adjusted to produce droplets of uniform size from the different fluidic circuits. In this manner, droplets produced from different fluidic circuits travel at the same velocity in a main channel and do not collide or coalesce in an unwanted manner. When the pressure is the variable parameter used for control, there is coupling between the aqueous and immiscible carrier fluid (e.g., oil) channels in an individual circuit. Therefore, any change to the aqueous pressure has an impact on the pressure at the nozzle and in turn affects the flow rate of the immiscible carrier fluid (IMF). For instance, increasing $P_{Aq}$, decreases $Q_{IMF}$ and vice-versa. Proper design of the resistances in both the aqueous and immiscible earner fluid channels controls the degree of coupling that can be expected when making a change to one or more of the input pressures. This in turn controls the sensitivity of the change in drop volume as a function of $P_A$.

Figure 3:
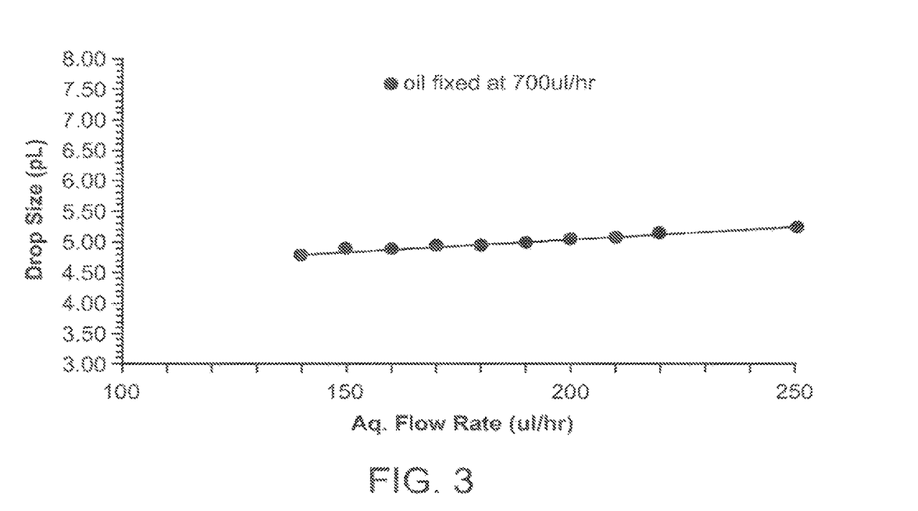
FIG. 3 is a graph showing droplet size sensitivity to changes in aqueous flow rate when using positive displacement pumping.
Figure 4:
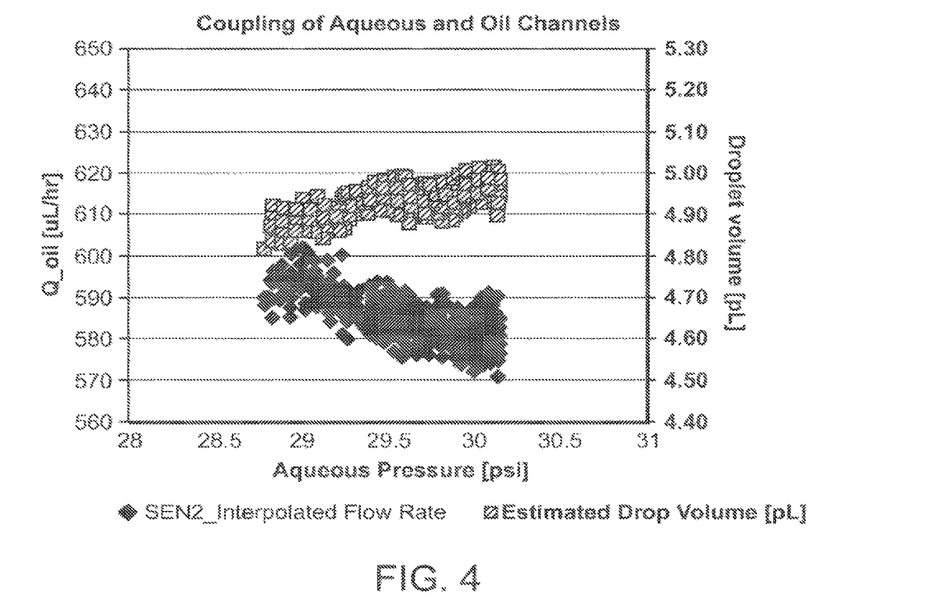
FIG. 4 is a graph showing droplet size sensitivity to changes in aqueous flow rate when using pressure driven pumping.

For comparison, the sensitivity of drop size to a change in flow rate is compared using both a positive displacement pump and a pressure driven system. FIG. 3 is a graph showing droplet size sensitivity to changes in aqueous flow rate when using positive displacement pumping. FIG. 4 is a graph showing droplet size sensitivity to changes in aqueous flow rate when using pressure driven pumping. Oil was used as the immiscible fluid for these comparisons. Using a similar chip with a similar circuit, a positive displacement pump yields a 10% change in drop volume when changing the flow rate by a factor of two. The pressure driven system yields a 2% change in drop volume for every psi of change in $P_A$. If the pressure was doubled, a 60% change in drop size could be expected when using the pressure driven system. Using a similar circuit, pressure gives 6× better control over the droplet volume when the aqueous channel is adjusted.

In certain embodiments, multiple fluidic circuits are used to produce droplets that all flow into a main channel. Proper design of die fluidic circuits, specifically by adjusting the fluidic resistance in both the aqueous and oil channels, controls the degree of influence that adjustments to the aqueous pressure has on each of the circuits, resulting in all of the circuits producing droplets of the same size. Changes in droplet size as a result of changes in pressure and flow rate can be modeled using the below calculations.

Figures 5, 6:
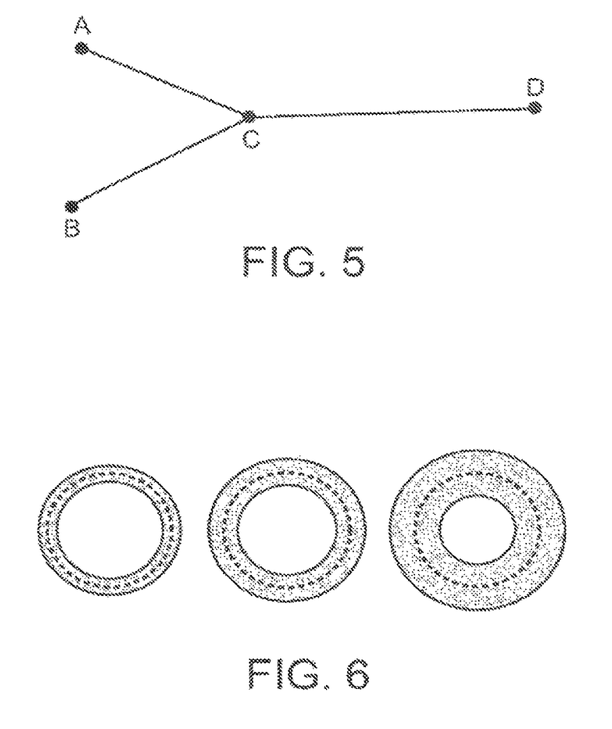
FIG. 5 shows a diagram of a single fluidic circuit.
FIG. 6 is a drawing illustrating that the same volume drop is subject to extreme changes in the lighting but the midpoint is always the same. From left to right, the intensity of the lighting decreases but the midpoint of the outline is always the same.

FIG. 5 shows a diagram of a single fluidic circuit for calculation purposes. One of skill in the an will recognize that the calculations shown herein may be applied to multiple fluidic circuits. (A) represents an immiscible carrier fluid channel, (B) represents an aqueous channel, (C) represents a junction of channels (A) and (B) where aqueous phase and immiscible carrier fluid phase meet to form droplets of the aqueous phase surrounded by the immiscible carrier fluid, and (D) represents outlet channel that receives the droplets. $P_A$ represents the pressure of the immiscible carrier fluid in the immiscible carrier fluid channel. $P_B$ represents the pressure of the aqueous fluid in the aqueous fluid channel $P_C$ represents the pressure at the junction of channels (A) and (B), $P_A$, and $P_C$ are ail greater than 0, and $P_D$ is equal to 0 because channel (D) is open to the atmosphere. $Q_{AC}$ represents the flow rate of the immiscible fluid, $Q_{BC}$ represents the flow rate of the aqueous fluid, and $Q_{CD}$ represents the flow rate of droplets in channel (D), $R_{AC}$ represents the fluid resistance in the immiscible carrier fluid channel $R_{BC}$ represents the fluidic resistance in the aqueous channel, and $R_{CD}$ represents the fluidic resistance in the (D) channel. Equations and expressions for $Q_{AC}$ and $Q_{BC}$ are as follows:

$$PA-PC=QAC(RAC) \quad \text{Equation 1;}$$

$$PB-PC=QBC(RBC) \quad \text{Equation 2; and}$$

$$PC=QCD(RCD)=(QAC+QBC)RCD \quad \text{Equation 3.}$$

Assuming that PA, PB, RAC, RBC, and RCD are known, then the three unknowns are PC, QAC, and QBC, OAC and QBC can be solved for as follows:

$$QAC = \frac{PA(RBC) + (PA - PB)RCD}{RAC(RBC) + RCD(RAC + RBC)} \quad \text{Equation 3}$$

and $$QBC = \frac{PB(RAC) + (PA - PB)RCD}{RAC(RBC) + RCD(RAC + RBC)}. \quad \text{Equation 4}$$

The sensitivities of the follow rates (Q) to changes in pressure (P) are determined by obtaining partial derivatives of QAC and QBC with respect to PA and PB, which yields:

$$\frac{\delta QA}{\delta PA} = \frac{(RBC + RCD)}{RAC(RBC) + RCD(RAC + RBC)};$$ Equation 5

$$\frac{\delta QA}{\delta PB} = \frac{RCD}{RAC(RBC) + RCD(RAC + RBC)};$$ Equation 6

$$\frac{\delta QB}{\delta PB} = \frac{(RAC + RCD)}{RAC(RBC) + RCD(RAC + RBC)};$$ Equation 7 and $$\frac{\delta QB}{\delta PA} = \frac{RCD}{RAC(RBC) + RCD(RAC + RBC)} = \frac{\delta QA}{\delta PB}.$$ Equation 8

Assuming that PA=PA+δPA then:

$$\frac{Q'AC}{QAC} = 1 + \frac{(RBC + RCD)\delta PA}{PA(RBC) + (PA - PB)RCD};$$ Equation 9 and $$\frac{Q'BC}{QBC} = 1 - \frac{(RCD)\delta PA}{PB(RAC) - (PA - PB)RCD}.$$ Equation 10

Similarly, assuming that F"B=PB+δB then:

$$\frac{Q''AC}{QAC} = 1 - \frac{(RCD)\delta PB}{PA(RBC) + (PA - PB)RCD};$$ Equation 11 and $$\frac{Q''BC}{QBC} = 1 + \frac{(RAC + RCD)\delta PB}{PB(RAC) - (PA - PB)RCD}.$$ Equation 12

Substituting chip dPCR 1,3 specifies into the above and assuming PA≈PB, thus neglecting PA−PB containing terms yields:

$$\frac{Q'A}{QA} = 1 + 1.4\frac{\delta PA}{PA};$$ Equation 13

$$\frac{Q'B}{QB} = -0.45\frac{\delta PA}{PA};$$ Equation 14

$$\frac{Q''A}{QA} = 1 - 0.36\frac{\delta PB}{PB};$$ Equation 15 and $$\frac{Q''B}{QB} = 1 + 3\frac{\delta PB}{PB}.$$ Equation 16

The results in FIG. 4 show that changing PA from 28 psi to 30 psi results in $Q_{BC}$ going from 577 μL/hr to 558 μL/hr, −3.3% change. The above model predicts a −3.1% change in $QB_1$ which is in agreement with the actually results data.

In certain embodiments, the system may be configured such that the circuits produce droplets of different size to allow for controlled droplet coalescence in the main channel. The fluidic circuits are arranged and controlled to produce an interdigitation of droplets of different sizes flowing through a channel. Such an arrangement is described for example in Link et al. (U.S. patent application numbers 2008/0014589, 2008/0003142, and 2010/0137163) and European publication number EP2047910 to Raindance Technologies Inc. Due to size variance, the smaller droplet will travel at a greater velocity than the larger droplet and will ultimately collide with and coalesce with the larger droplet to form a mixed droplet.

Another benefit of the added resistance in both channels next to the nozzle occurs during priming. Simultaneous arrival of both the aqueous and carrier liquids is difficult to produce reliably. If the carrier fluid enters the aqueous channel and travels all the way back into the filter elements, the aqueous and carrier liquids begin to mix and emulsify before the nozzle. This mixing interference causes significant variability in the size of the generated droplets. The added resistance nest to the nozzle eliminates, the mixing interference by creating a path, of relatively high resistance without emulsifying features that are in the filter. Therefore, if the carrier fluid arrives at the nozzle first it will, travel both into the aqueous resistor and towards the outlet of the chip. The outlet of the chip has a resistance that is much smaller than the aqueous resistor and therefore the majority of the carrier fluid will flow in that direction. This gives the aqueous liquid time to reach the nozzle before the carrier fluid enters the filter feature.

Droplet Measurement

Figure 7A:
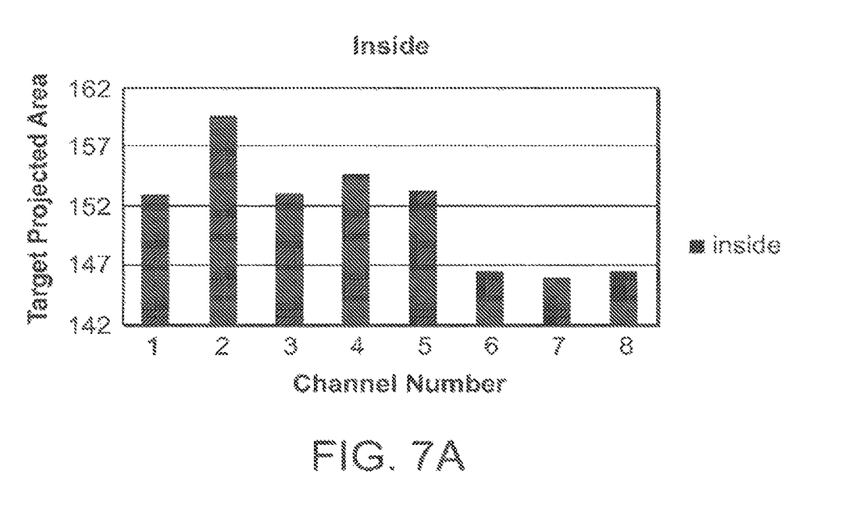
FIGS. 7A-C provides three graphs that demonstrate the differences in the droplet measuring techniques, and the projected area required to produce 5 pL drops when using the inside, outside and midpoint of a droplet image.
Figure 7B:
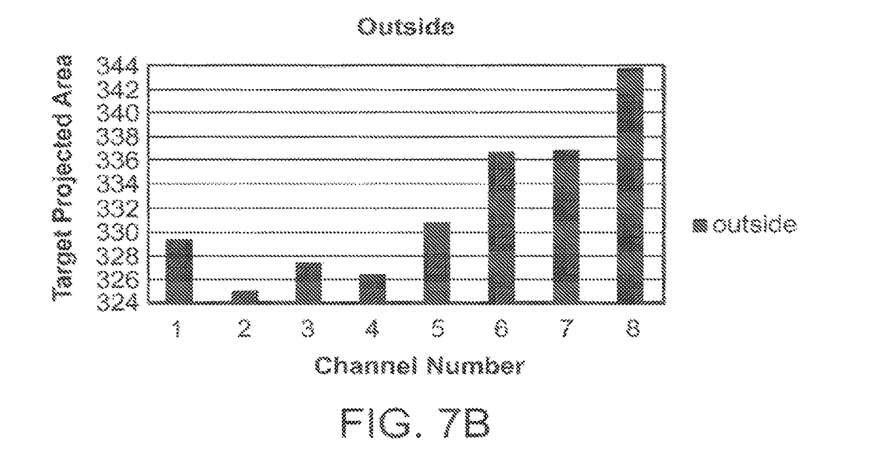
Figure 7C:
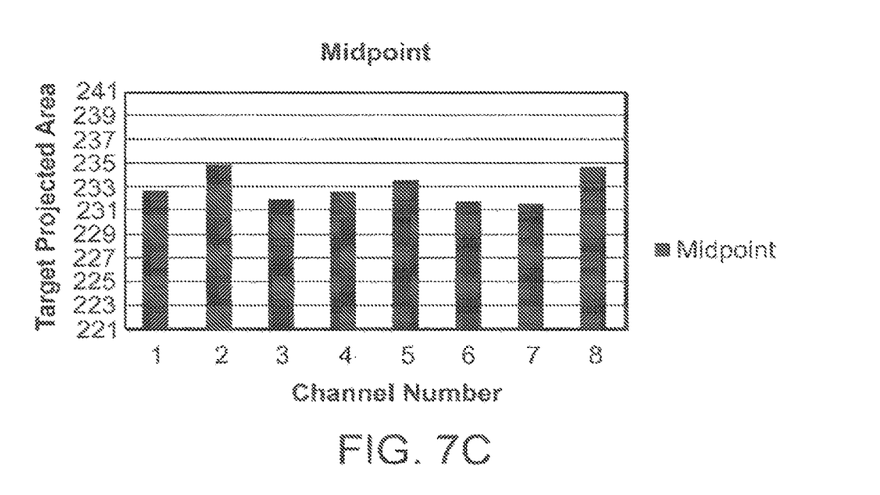
Figure 8:
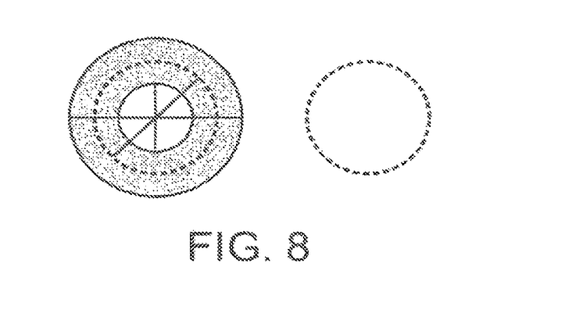
FIG. 8 is a schematic illustrating measurement of droplet size using the midpoint technique described herein.

The volume of an individual droplet is measured using real-time image analysis. This in turn is fed back into a control loop where a known projected area is targeted and equal to a given droplet volume. Microfluidic chips are calibrated using a 3 point reference emulsion of know volumes to generate calibration curves for each channel. The idea is that the midpoint of the outline of a projected droplet image is always the same regardless of the lighting. This demonstrated in FIG. 6, which is a drawing illustrating that the same volume drop is subject to extreme changes in the lighting but the midpoint is always the same. From left to right, the intensity of the lighting decreases but the midpoint of the outline is always the same. In contrast to determining the projected area of the inside of the drop, which is difficult due to chip and lighting imperfections and variability, or the outside of the drop, which is also quite sensitive to lighting and chip imperfections, methods of the invention use the midpoint of the outline of a projected droplet image, which is always the same regardless of the lighting and chip imperfections. Using the midpoint "flattens out" the imperfections and is significantly less sensitive to outside influences on projected drop size. FIGS. 7A-C provides three graphs that demonstrate the differences in the droplet measuring techniques, and the projected area required to produce 5 pL drops when using the inside, outside and midpoint of a droplet image. Finding both the outside and inside projected area allows you calculate the outside and inside diameters. Calculating the average of the outside and inside diameters gives you the midpoint diameter. From there an estimated projected area is calculated from the midpoint diameter (See FIG. 8).

Nucleic Acid Target Molecules

One of skill in the art will recognize that methods and systems of the invention are not limited to any particular type of sample, and methods and systems of the invention may be used with any type of organic, inorganic, or biological molecule. In particular embodiments the droplets include nucleic acids. Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and nontemplate nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loopstructures).

Target Amplification

Methods of the invention further involve amplifying a target nucleic acid(s) in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview. N.Y. [1995]. The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyperbranched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification.

The process for amplifying the target sequence includes introducing an excess of oligonucleotide primers so a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The sample droplet may be pre-mixed with a primer or primers and other reagents for on amplification reaction, or the primer or primers and other reagents for an amplification reaction may be added to the droplet. In some embodiments, fluidic circuits are controlled to produce droplets of different sizes to result in controlled merging of droplets. In those embodiments, sample droplets are created by segmenting the starting sample and merging that droplet with a second set of droplets including one or more primers for the target nucleic acid in order to produce final droplets. The merging of droplets can be accomplished using, for example, one or more droplet merging techniques described for example in link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. A first droplet formation module produces the sample droplets that on average contain a single target nucleic acid. A second droplet formation module produces droplets that contain reagents for a PCR reaction. Such droplets generally include Taq polymerase, deoxynucleotides of type A, C, G and T, magnesium chloride, and forward and reverse primers, all suspended within an aqueous buffer. The second droplet also includes detectably labeled probes for detection of the amplified target nucleic acid, the details of which are discussed below. In embodiments that start with a pre-mix of sample and reagents for a PCR reaction, the pre-mix includes all of the above described components.

The droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes Taq polymerase, deoxynucleotides of type A, C, G and T, magnesium chloride, forward and reverse primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/001458, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAs is from Hitachi Software Engineering. The TM (melting or annealing temperature) of each primer is calculated using software programs such as Oligo Design, available from Invitrogen Corp.

Once final droplets have been produced, the droplets are thermal cycled, resulting in amplification of the target nucleic acid in each droplet. In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used tor the amplification reaction. The three temperature zones are controlled to result in denaturation of double stranded nucleic acid (high temperature zone), annealing of primers (low temperature zones), and amplification of single stranded nucleic acid, to produce double stranded nucleic acids (intermediate temperature zones). The temperatures within these zones fall within ranges well known in the art for conducting PCR reactions, See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the higher temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids tinder go the same thermal cycling and chemical reaction as the droplets passes through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

Target Detection

After amplification, droplets are flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in link et al. (U.S. patent application numbers 2008/0014589, 2008/0003142, and 2010/0137163) and European publication number EP2047910 to Raindance Technologies Inc.

In certain embodiments, amplified target are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4'6-diamimdino-2-phenylindole (DAPI); 5'5"-dibromopyrogallol-sulfonaphthalein (Bromopyrogallol Red); 7-diethylamino-3-(4'-isothiocyanatophenyl)-4-methylcumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives; pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

During amplification, fluorescent signal is generated in a TaqMan assay by the enzymatic degradation of the fluorescently labeled probe. The probe contains a dye and quencher that are maintained in close proximity to one another by being attached to the same probe. When in close proximity, the dye is quenched by fluorescence resonance energy transfer to the quencher.

Certain probes are designed that hybridize to the wild-type of the target, and other probes are designed that hybridize to a variant of the wild-type of the target. Probes that hybridize to the wild-type of the target have a different fluorophore attached than probes that hybridize to a variant of the wild-type of the target. The probes that hybridize to a variant of the wild-type of the target are designed to specifically hybridize to a region in a ICR product that contains or is suspected to contain a single nucleotide polymorphism or small insertion or deletion.

During the PCR amplification, the amplicon is denatured allowing the probe and PCR primers to hybridize. The PCR primer is extended by Taq polymerase replicating the alternative strand. During the replication process the Taq polymerase encounters the probe which is also hybridized to the same strand and degrades it. This releases the dye and quencher from the probe which are then allowed to move away from each other. This eliminates the FRET between the two, allowing the dye to release its fluorescence. Through each cycle of cycling more fluorescence is released. The amount of fluorescence released depends on the efficiency of the PCR reaction and also the kinetics of the probe hybridization. If there is a single mismatch between the probe and the target sequence the probe will not hybridize as efficiently and thus a fewer number of probes are degraded during each round of PCR and thus less fluorescent signal is generated. This difference in fluorescence per droplet can be detected and counted. The efficiency of hybridization can be affected by such things as probe concentration, probe ratios between competing probes, and the number of mismatches present in the probe.

Droplet Sorting

Methods of the invention may further include sorting the droplets. A sorting module may be a junction of a channel where the flow of droplets can change direction to enter one or more other channels, e.g., a branch channel, depending on a signal received in connection with a droplet interrogation in the detection module. Typically, a sorting module is monitored and/or under the control of the detection module, and therefore a sorting module may correspond to the detection module. The sorting region is in communication with and is influenced by one or more sorting apparatuses.

A sorting apparatus includes techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A branch channel is a channel that is in communication with a sorting region and a main channel. The main channel can communicate with two or more branch channels at the sorting module or branch point, forming, for example, a T-shape or a Y-shape. Other shapes and channel geometries may be used as desired. Typically, a branch channel receives droplets of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In certain embodiments, a fluidic droplet is sorted or steered by inducing a dipole in the uncharged fluidic droplet (which may be initially charged or uncharged), and sorting or steering the droplet using an applied electric field. The electric field may be an AC field, a DC field, etc. For example, a channel containing fluidic droplets and carrier fluid, divides into first and second channels at a branch point. Generally, the fluidic droplet is uncharged. After the branch point, a first electrode is positioned near the first channel, and a second electrode is positioned near the second channel. A third electrode is positioned near the branch point of the first and second channels. A dipole is then induced in the fluidic droplet using a combination of the electrodes. The combination of electrodes used determines which channel will receive the flowing droplet. Thus, by applying the proper electric field, the droplets can be directed to either the first or second channel as desired. Further description of droplet sorting is shown for example in Link et al. (U.S. patent application numbers 2008/0014589, 2008/0003142, and 2010/0137163) and European publication number EP2047910 to Raindance Technologies Inc.

Release From Droplets

Methods of the invention may further involve releasing the enzymes from the droplets for further analysis. Methods of releasing contents from the droplets are shown for example in Link et al. (U.S. patent application numbers 2008/0014589, 2008/0003142, and 2010/0137163) and European publication number EP2047910 to Raindance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second earner fluid which contains a destabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

Microfluidic Chips

Figure 9:
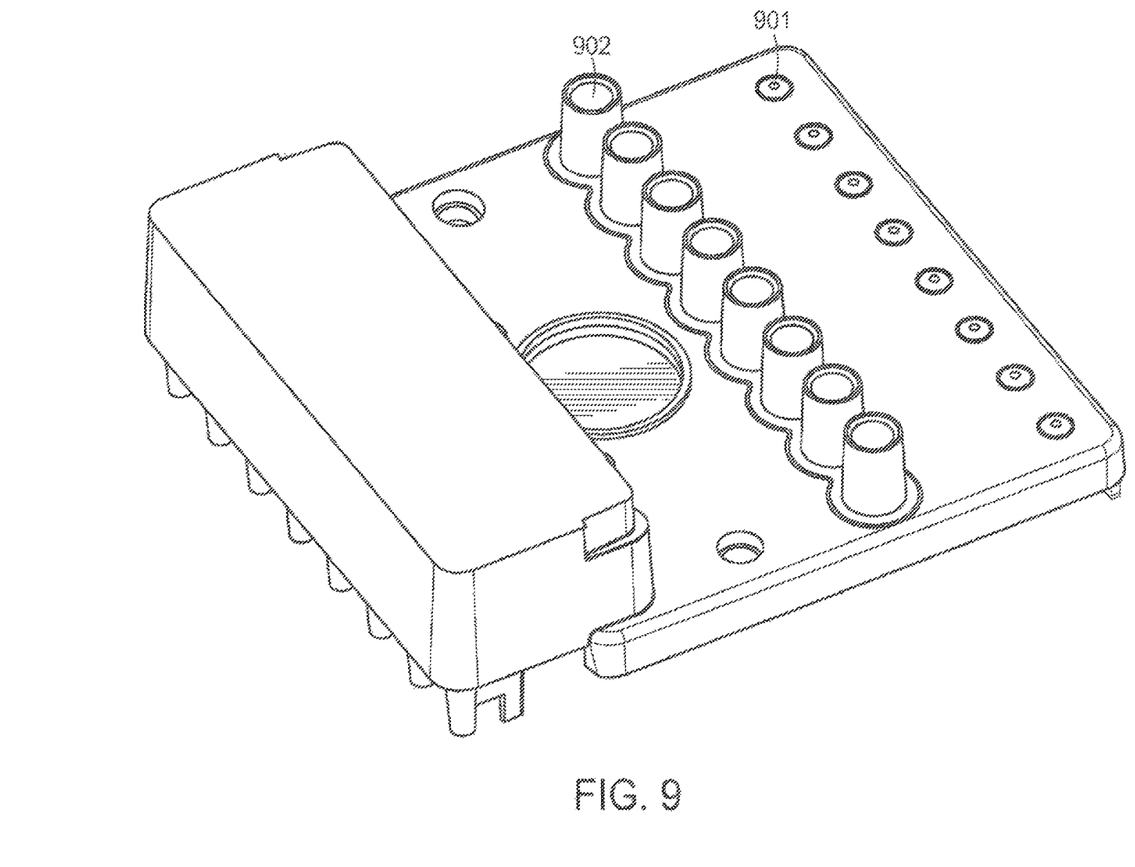
FIG. 9 is a schematic diagram showing a microfluidic interconnect as described in the Specification, containing a plurality of aqueous fluid ports and an immiscible fluid port for use in methods of the invention.
Figure 10:
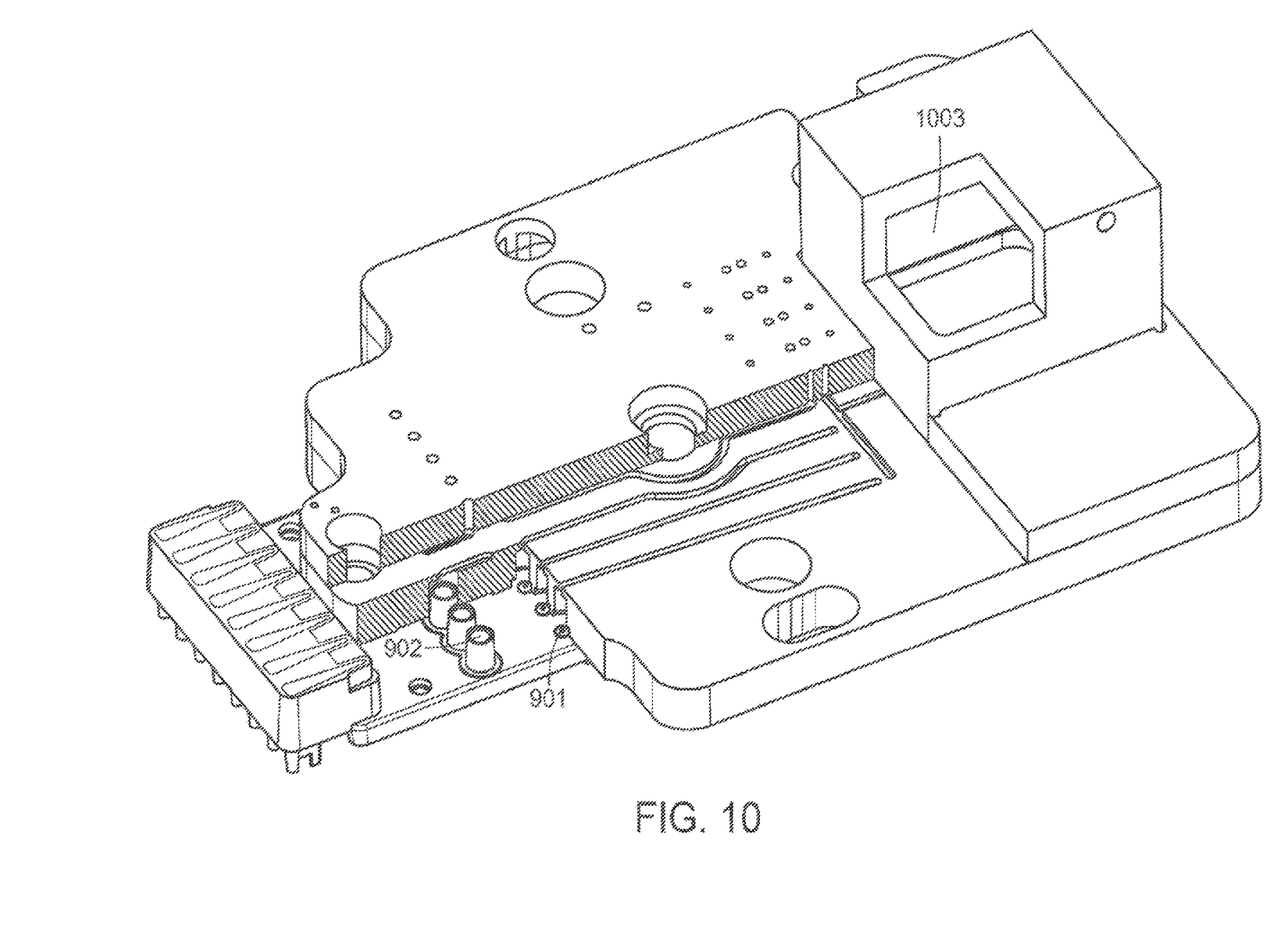
FIG. 10 is a schematic diagram showing an apparatus as described in the Specification showing the microfluidic interconnect shown in FIG. 9 with a manifold overlay and immiscible fluid storage.
Figure 11:
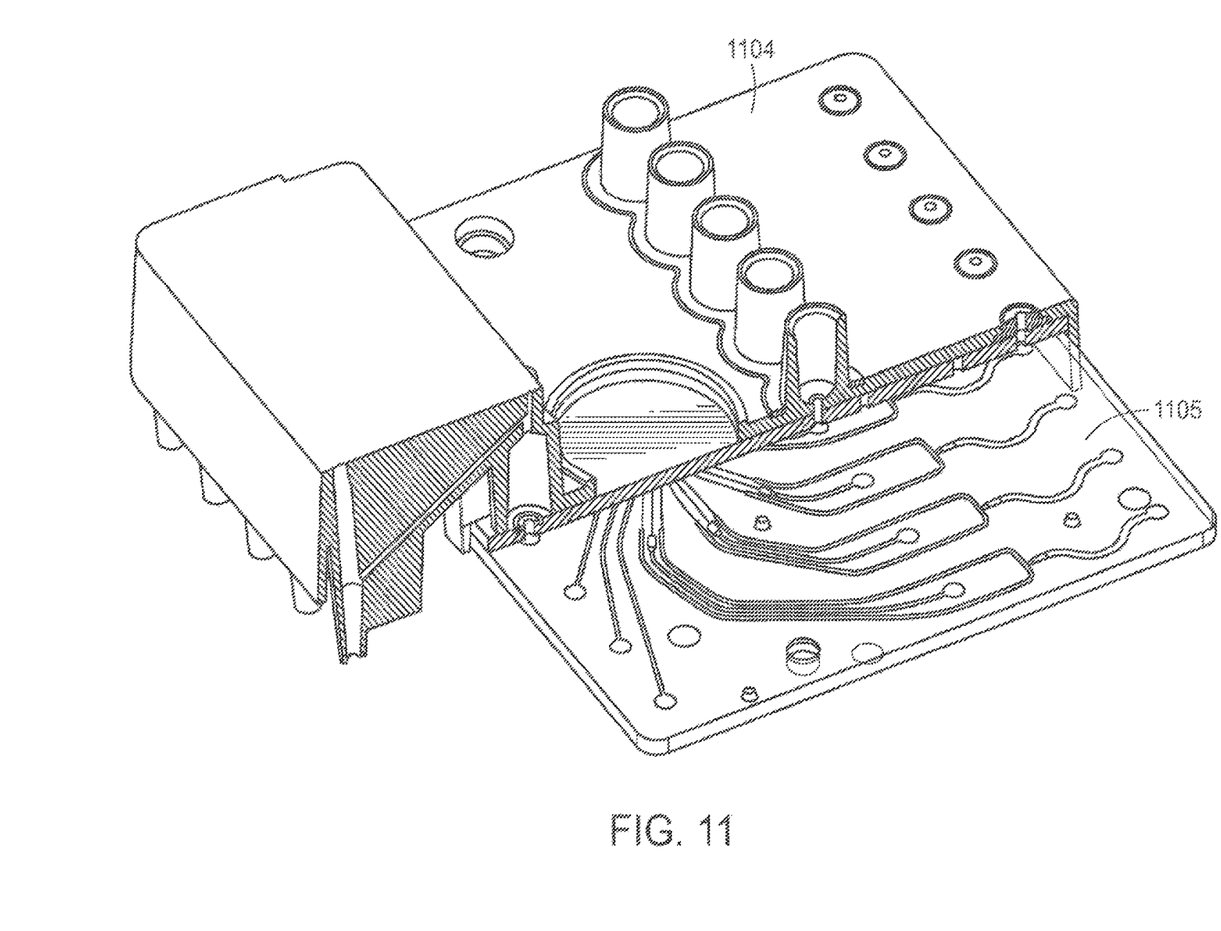
FIG. 11 is a schematic diagram showing the relationship between the microfluidic interconnect of FIG. 9 with a microfluidic chip for use in methods of the invention.

Microfluidic chips for performing biological, chemical, and diagnostic assays are described in U.S. Published Patent Application No. US2008/0003142 and US2008/0014589, the content of each of which is incorporated by reference herein in its entirety. Such microfluidic devices generally include at least one substrate having one or more microfluidic channels etched or molded into the substrate, and one or mote interconnects (fluid interface). The one or more interconnects contain inlet modules that lead directly into the microfluidic channels, and serve to connect the microfluidic channel to a means for introducing a sample fluid to the channel. The one or more interconnects also serve to form a seal between the microfluidic substrate and the means for introducing a sample. The one or more interconnects can be molded directly into the microfluidic substrate, as one or more individual pieces, or as a single, monolithic self-aligning piece. The interconnect may also be a separate piece and the entire assembly (the manifold, microfluidic chip, and interconnect) can be modular as well. An exemplary interconnect is shown in FIG. 9, which shows the interconnect with immiscible fluid port 901 and aqueous fluid port 902. FIG. 10 shows the interconnect integrated with a manifold having oil reservoir 1003 and a microfluidic chip thereunder. FIG. 11 shows the interconnect 1104 integrated with a microfluidic chip 1105 with the manifold (not shown) removed.

Microfluidic chips according to the invention include a substrate defining at least one internal channel and at least one port in fluid communication with the channels. In one particular embodiment, a chip of the invention includes a top plate adhered to a bottom plate to form the substrate with the channel(s) and port(s). The top plate can include the port(s), and the bottom plate can include the channel(s), such that when these two plates are brought together and adhered to each other the combination forms the substrate with the channel(s) and the port(s). The microfluidic chip can be injection molded from a variety of materials. Preferably the microfluidic chip is injection molded using a cyclic olefin copolymer (COC) or cyclic olefin polymer (COP) or blend of COC and COP.

Chips of the invention include one or more fluidic circuits. Each circuit including a sample fluid channel, an immiscible carrier fluid channel, and an outlet channel. The channels of each circuit are configured such that they meet at a junction so that droplets of aqueous fluid surrounded by carrier fluid are formed at the junction an flow into the outlet channel. The outlet channel of each circuit is connected to a main channel that receives all of the droplets from the different fluidic circuits and flows the droplets to different modules in the chip for analysis. In certain embodiments, each fluid circuit carries a different aqueous sample fluid in order to produce different sample droplets. In other embodiments, the fluidic circuits all carry the same aqueous sample fluid, and thus produce the same sample droplets.

A pressure source, optionally coupled to electronic pressure regulators, is used to pump fluids through multiple microfluidic channels in parallel. Multiple pressure regulators control the aqueous inputs. The immiscible carrier fluid input is under gain control for all channels simultaneously. In this configuration, there is independent control of individual circuits to adjust projected area to obtain a target droplet volume. Droplet volume is measured either relatively or absolutely (depending on the application) via real-time image analysis. Proper design of the microfluidic circuits is required to obtain sensitive and precise control of the droplet volume in all channels.

Pressure driven flow allows for the replacement of expensive mechanical parts with inexpensive pneumatic control products. Pressure driven flow is instantaneous and pulse-free. Taking advantage of circuits in parallel, constant pressure driven flow instantly adjusts to changes in resistance in any and all channels without affecting any of the other channels. Any pressure sources known in the art may be used with chips of the invention. In certain embodiments, the pressure source is coupled to electronic regulators. When coupled to an electronic regulator, the pressure source may be an external compressor with a reservoir for pumping compressed nitrogen, argon or air. In embodiments that do not used electronic regulators, an internal air cylinder with a linear actuator is applied.

The regulators should be of a type capable of regulating gas pressure from about 0 to about 5 atm in 100 evenly spaced increments (0-10 V, step=0.1 V). Each aqueous input is independently driven and controlled by a separate pressure regulator. The immiscible fluid lines are controlled in a gain control fashion, where one regulator is used to drive and control the flow of immiscible fluid through the entire system.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method of analyzing a microdroplet, comprising:
   forming a microdroplet in a microfluidic channel;
   obtaining a projected image of the microdroplet in the microfluidic channel, wherein the image includes a microdroplet outline;
   measuring an outside diameter of the microdroplet outline;
   measuring an inside diameter of the microdroplet outline;

analyzing the size of the microdroplet by using a midpoint diameter of the microdroplet outline, wherein the midpoint diameter is the average of the outside diameter and the inside diameter; and adjusting pressure inside the microfluidic channel to alter the size of the microdroplet.

2. The method of claim 1, further comprising generating a calibration curve for the size of the microfluidic channel, and using the calibration curve in analyzing the size of the microdroplet.

3. The method of claim 2, wherein the microfluidic channel is measured with a plurality of reference microdroplets of known volumes.

4. The method of claim 1, wherein the microdroplet comprises an aqueous fluid surrounded by an immiscible carrier fluid.

5. The method of claim 4, wherein the carrier fluid is a fluorocarbon oil.

6. The method of claim 4, wherein the carrier fluid comprises a first surfactant.

7. The method of claim 6, wherein the first surfactant is a fluoro surfactant.

8. The method of claim 6, wherein the aqueous fluid comprises a second surfactant.

9. The method of claim 1, further comprising flowing a plurality of microdroplets in the microfluidic channel, and obtaining an image of each microdroplet in the microfluidic channel.

10. The method of claim 9, wherein the plurality of microdroplets travel at the same velocity.

11. The method of claim 9, wherein the plurality of microdroplets travel at different velocities.

12. The method of claim 9, wherein the plurality of microdroplets are of substantially similar size.

13. The method of claim 9, wherein the plurality of microdroplets are of different sizes.

14. The method of claim 9, wherein the aqueous fluid comprises a sample.

15. The method of claim 14, wherein the sample is a target nucleic acid.

16. The method of claim 15, wherein the aqueous fluid further comprises a primer and reagents for an amplification reaction.

17. The method of claim 16, wherein the amplification reaction is a polymerase chain reaction (PCR).

18. The method of claim 1, further comprising obtaining feedback from the projected image.

19. The method of claim 18, further comprising adjusting the size of the droplet after obtaining the feedback.

* * * * *